US009410885B2

(12) United States Patent
Schober et al.

(10) Patent No.: US 9,410,885 B2
(45) Date of Patent: Aug. 9, 2016

(54) ATOMIC SENSOR PHYSICS PACKAGE HAVING OPTICALLY TRANSPARENT PANES AND EXTERNAL WEDGES

(71) Applicant: Honeywell International Inc., Morristown, NJ (US)

(72) Inventors: Christina Marie Schober, St. Anthony, MN (US); James A. Vescera, Hopkins, MN (US); Jennifer S. Strabley, Maple Grove, MN (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 13/947,633

(22) Filed: Jul. 22, 2013

(65) Prior Publication Data

US 2015/0022816 A1    Jan. 22, 2015

(51) Int. Cl.
*G01N 21/00* (2006.01)
*G01N 21/59* (2006.01)
*G01D 11/24* (2006.01)
*G04F 5/14* (2006.01)
*G01J 5/04* (2006.01)
(Continued)

(52) U.S. Cl.
CPC ............ *G01N 21/59* (2013.01); *G01D 11/245* (2013.01); *G04F 5/14* (2013.01); *G01J 5/045* (2013.01); *G01L 19/144* (2013.01); *H05H 7/14* (2013.01); *Y10T 29/49002* (2015.01)

(58) Field of Classification Search
CPC ..... G01J 5/045; G01L 19/144; G01D 11/245; H05H 7/14
See application file for complete search history.

(56) References Cited

U.S. PATENT DOCUMENTS

| 4,817,112 A | 3/1989 | Weber et al. |
| 4,983,844 A * | 1/1991 | Korevaar ...................... 250/382 |

(Continued)

FOREIGN PATENT DOCUMENTS

| DE | 3830149 | 3/1990 |
| EP | 2154585 | 2/2010 |

(Continued)

OTHER PUBLICATIONS

U.S. Patent and Trademark Office, "Office Action", "from U.S. Appl. No. 13/362,286", Dec. 19, 2013, pp. 1-12, Published in: US.
(Continued)

*Primary Examiner* — Kara E Geisel
*Assistant Examiner* — Hina F Ayub
(74) *Attorney, Agent, or Firm* — Fogg & Powers LLC (57) ABSTRACT

One embodiment is directed towards a physics package of an atomic sensor. The physics package includes a plurality of panes of optically transparent material enclosing a vacuum chamber and one or more wedges attached to an external surface of one or more of the panes. The physics package also includes at least one of a light source, photodetector, or mirror attached to the one or more wedges, the light source configured to generate an input light beam for the vacuum chamber, the photodetector configured to detect an output light beam from the vacuum chamber, and the mirror configured to reflect a light beam from the vacuum chamber back into the vacuum chamber, wherein the wedge is configured to oriented such a light source, photodetector, or mirror such that a respective light beam corresponding thereto transmits through a corresponding pane at an acute angle with respect to the corresponding pane.

20 Claims, 5 Drawing Sheets

(51) Int. Cl.
*G01L 19/14* (2006.01)
*H05H 7/14* (2006.01)

(56) References Cited

U.S. PATENT DOCUMENTS

| | | | |
|---|---|---|---|
| 5,010,251 A * | 4/1991 | Grinberg et al. | 250/332 |
| 5,058,124 A | 10/1991 | Cameron et al. | |
| 5,327,105 A | 7/1994 | Liberman et al. | |
| 5,528,028 A | 6/1996 | Chu et al. | |
| 5,594,843 A * | 1/1997 | O'Neill | 345/427 |
| 6,215,366 B1 | 4/2001 | Kern et al. | |
| 6,303,928 B1 | 10/2001 | Buell et al. | |
| 6,406,578 B1 | 6/2002 | Schober et al. | |
| 6,570,459 B1 | 5/2003 | Nathanson et al. | |
| 6,772,630 B2 | 8/2004 | Araya | |
| 6,837,075 B1 | 1/2005 | Snowdon et al. | |
| 6,895,164 B2 * | 5/2005 | Saccomanno | 385/146 |
| 6,900,702 B2 | 5/2005 | Youngner et al. | |
| 7,323,941 B1 | 1/2008 | Happer et al. | |
| 7,379,486 B2 | 5/2008 | Lust et al. | |
| 7,446,618 B2 | 11/2008 | Koyama | |
| 7,468,637 B2 | 12/2008 | Braun et al. | |
| 7,549,866 B2 * | 6/2009 | Cohen et al. | 434/267 |
| 7,619,485 B2 | 11/2009 | DeNatale et al. | |
| 7,707,891 B2 * | 5/2010 | Antila et al. | 73/714 |
| 7,944,317 B2 | 5/2011 | Strabley et al. | |
| 7,965,147 B2 | 6/2011 | Strabley et al. | |
| 8,071,019 B2 | 12/2011 | Touchberry et al. | |
| 2004/0040658 A1 * | 3/2004 | Usui et al. | 156/345.24 |
| 2006/0022761 A1 | 2/2006 | Abeles et al. | |
| 2006/0051883 A1 | 3/2006 | Mescher et al. | |
| 2006/0220524 A1 * | 10/2006 | Jeon et al. | 313/495 |
| 2007/0034809 A1 | 2/2007 | Lal et al. | |
| 2007/0200643 A1 | 8/2007 | Dimarcq et al. | |
| 2008/0267232 A1 | 10/2008 | DeNatale | |
| 2010/0033255 A1 | 2/2010 | Strabley et al. | |
| 2010/0033256 A1 | 2/2010 | Strabley et al. | |
| 2010/0102893 A1 | 4/2010 | Chindo et al. | |
| 2010/0111750 A1 | 5/2010 | Touchberry et al. | |
| 2010/0188661 A1 * | 7/2010 | Cole | 356/437 |
| 2011/0013179 A1 * | 1/2011 | Meijer et al. | 356/217 |
| 2013/0194046 A1 | 8/2013 | Schober et al. | |
| 2014/0096607 A1 | 4/2014 | Schober et al. | |

FOREIGN PATENT DOCUMENTS

| | | |
|---|---|---|
| JP | 61144613 | 2/1986 |
| WO | 2009025893 | 2/2009 |

OTHER PUBLICATIONS

Japanese Patent Office, "Notice of Allowance from JP Application No. 2009-184461 mailed Apr. 16, 2014", "from Foreign Counterpart of U.S. Appl. No. 12/484,878", Apr. 16, 2014, pp. 1-4, Published in: JP.

U.S. Patent and Trademark Office, "Office Action", "U.S. Appl. No. 13/362,286", Aug. 16, 2013, pp. 1-23.

Japanese Patent Office, "Office Action", "from Foreign Counterpart of U.S. Appl. No. 12/484,878", Sep. 6, 2013, pp. 1-6, Published in: JP.

Schober et al, "Systems and Methods for External Frit Mounted Components", "U.S. Appl. No. 13/362,286, filed Jan. 31, 2012", , pp. 1-22.

European Patent Office, "Communication under Rule 71(3) EPC", "from Foreign Counterpart of U.S. Appl. No. 12/484,878", Jul. 2, 2012, pp. 1-8.

U.S. Patent and Trademark Office, "Notice of Allowance", "U.S. Appl. No. 12/484,878", Apr. 8, 2011, pp. 1-18.

European Patent Office, "Office Action", "from Foreign Counterpart of U.S. Appl. No. 13/362,286", May 7, 2013, pp. 1-5, Published in: EP.

European Patent Office, "European Search Report", "from Foreign Counterpart of U.S. Appl. No. 13/362,286", Apr. 18, 2013, pp. 1-3, Published in: EP.

Ben-Aroya et al., "A CPT-Based RB Atomic Clock Employing a Small Spherical Glass Vapor Cell", "38th Annual Precise Time and Time Interval Meeting", Jul. 2007, pp. 259-270.

Shober et al., "Systems and Methods for External Frit Mounted Components", "U.S. Appl. No. 13/362,286,", Jan. 31, 2012, pp. 1-22.

Iga et al., "Stacked Planar Optics: an Application of the Planar Microlens", "Applied Optics", Oct. 1, 1982, pp. 3456-3460, vol. 21, No. 19.

Kitching, "Time for a Better Receiver: Chip-Scale Atomic Frequency References", "GPS World", Nov. 2007, pp. 1-6.

Knappe et al., "Microfabricated Atomic Clocks and Magnetometers", "Journal of Optics A: Pure and Applied Optics", May 2006, pp. S318-S322.

Knappe et al., "Advances in Chip-Scale Atomic Frequency References at NIST", "Proc. of SPIE ", 2007, pp. 1-10, vol. 6673.

Knappe, "A microfabricated atomic clock", "Applied Physics Letters", Aug. 30, 2004, pp. 1460-1462, vol. 85, No. 9, Publisher: American Institute of Physics.

Kohel et al., "Quantum Gravity Gradiometer Development for Space", "http://esto.nasa.gov/conferences/ESTC2006/papers/b4p1. pdf", Jun. 28, 2006, pp. 1-7.

Oikawa et al., "Optical Tap Array Using Distributed-Index Planar Microlens", "Electronics Letters", Apr. 15, 1982, pp. 316-317, vol. 18, No. 8.

Sander et al., "Magnetoencephalography with a Chip-Scale Atomic Magnetometer", "Biomedical Optics Express", Apr. 2012, pp. 981-990, vol. 3, No. 5.

Schober et al., "Systems and Methods for Gettering an Atomic Sensor", "U.S. Appl. No. 13/231,438", Sep. 13, 2011, pp. 1-17.

U.S. Patent and Trademark Office, "Notice of Allowance", "from U.S. Appl. No. 13/362,286", Jun. 13, 2014, pp. 1-10, Published in: US.

European Patent Office, "Office Action from EP Application No. 14167394.7 mailed Mar. 10, 2015", "from Foreign Counterpart of U.S. Appl. No. 13/947,633", Mar. 10, 2015, pp. 1-7, Published in: EP.

Nelson et al., "Cold Atom Micro Primary Standard (CAMPS)", "IEEE/ION Position Location and Navigation Symposium (PLANS)", Apr. 23, 2012, pp. 1094-1098, Publisher: IEEE.

U.S. Patent and Trademark Office, "Notice of Allowance and Fee(s) Due", "U.S. Appl. No. 13/644,618", Nov. 10, 2015, pp. 1-9.

U.S. Patent and Trademark Office, Office Action, U.S. Appl. No. 13/644,618, Jul. 13, 2015, pp. 1-53.

* cited by examiner

ATOMIC SENSOR PHYSICS PACKAGE HAVING OPTICALLY TRANSPARENT PANES AND EXTERNAL WEDGES

STATEMENT REGARDING FEDERALLY SPONSORED RESEARCH OR DEVELOPMENT

This invention was made with Government support under W31P4Q-09-C-0348 awarded by DARPA. The Government has certain rights in the invention.

BACKGROUND

Efforts are being made to reduce the size and packaging of atomic sensors, including atomic clocks and other sensors which utilize cold atom clouds as the sensing element. To accomplish this, efforts are focusing on reducing the size of the physics package for the atomic sensor. One example of a physics package is a glass block that is machined and sealed to maintain an ultra-high vacuum. In certain configurations, the glass block includes a plurality of faces on its exterior and a plurality of angled borings that serve as light paths to trap, cool, and manipulate the cold atomic sample. Mirrors and windows are fixedly attached over the exterior openings of the light path bores to seal the physics package. A cavity evacuation structure (e.g., vacuum pumping port) is attached to provide means for initial vacuum evacuation of the physics package. A sample reservoir (e.g., a reservoir for alkali material) is attached to supply the atoms that will be used in the sensor. The sample reservoir is broken or otherwise activated after vacuum processing, releasing a background vapor. Atoms in the background vapor are cooled by the optical beams and trapped by magnetic fields in a configuration commonly called a magneto optical trap (MOT) or without the magnetic field, an optical molasses. When cooling atoms from a background vapor, the number of atoms collected into the MOT scales as the fourth power of the optical beam size used in the physics package. In the fundamental limit, the signal to noise of atomic sensors scale as the square root of the trapped atoms, lending a fundamental scaling on the sensor signal to noise and optical beam size. Developing a small volume physics package which allows for large optical beams and added-flexibility of a multi-beam configuration is critical to the development of high performance miniature atomic physics packages. Using multiple beam MOT configuration allow flexibility that a single beam configuration, such as a pyramid trap, does not allow. This flexibility is necessary, for example, to consider atomic sensor or clocks which require optical pumping for precision state preparation, optical pulses for coherent atomic manipulation or atomic "beam splitters", or for reduction of optical scatter via the selective shuttering of optical beams.

SUMMARY

One embodiment is directed towards a physics package of an atomic sensor. The physics package includes a plurality of panes of optically transparent material enclosing a vacuum chamber and one or more wedges attached to an external surface of one or more of the panes. The physics package also includes at least one of a light source, photodetector, or mirror attached to the one or more wedges, the light source configured to generate an input light beam for the vacuum chamber, the photodetector configured to detect an output light beam from the vacuum chamber, and the mirror configured to reflect a light beam from the vacuum chamber back into the vacuum chamber, wherein the wedge is configured to oriented such a light source, photodetector, or mirror such that a respective light beam corresponding thereto transmits through a corresponding pane at an acute angle with respect to the corresponding pane.

DRAWINGS

Understanding that the drawings depict only exemplary embodiments and are not therefore to be considered limiting in scope, the exemplary embodiments will be described with additional specificity and detail through the use of the accompanying drawings, in which.

In accordance with common practice, the various described features are not drawn to scale or with exact angles, but are drawn to emphasize specific features relevant to the exemplary embodiments.

DETAILED DESCRIPTION

As the size of the glass block described above is further reduced, however, the glass can become too fragile to make multiple beam bores through the block, resulting in breakage, fractures, and/or chips when machining the bores in the glass block. For sensors using laser cooled atoms from a vapor, this issue is compounded by the desire to make the bore sizes as large as possible to accommodate large optical beams.

The subject matter described herein can address these issues by providing a physics package composed of a plurality of panes of optically transparent material (e.g., glass) disposed in a simple geometry, with one or more light sources, photodetectors, and/or mirrors attached to the exterior of the panes. A prism can be placed and physically adhered between some or all of the light source(s), photodetector(s), and/or mirror(s) and its respective pane to steer a light beam in a desired direction. The light source(s), photodetector(s), mirror(s), and/or prism(s) can be attached after construction of the vacuum chamber enabling for post construction alignment. Additionally, the prisms enable the ability to orient light paths entering and exiting a pane at acute angles with respect to the pane. These attributes enable the vacuum chamber to be constructed with a geometry that has excellent strength while allowing for large optical beams and a large vacuum chamber, enabling the physics package to achieve a small size without compromising performance or operational flexibility.

Figure 1A:
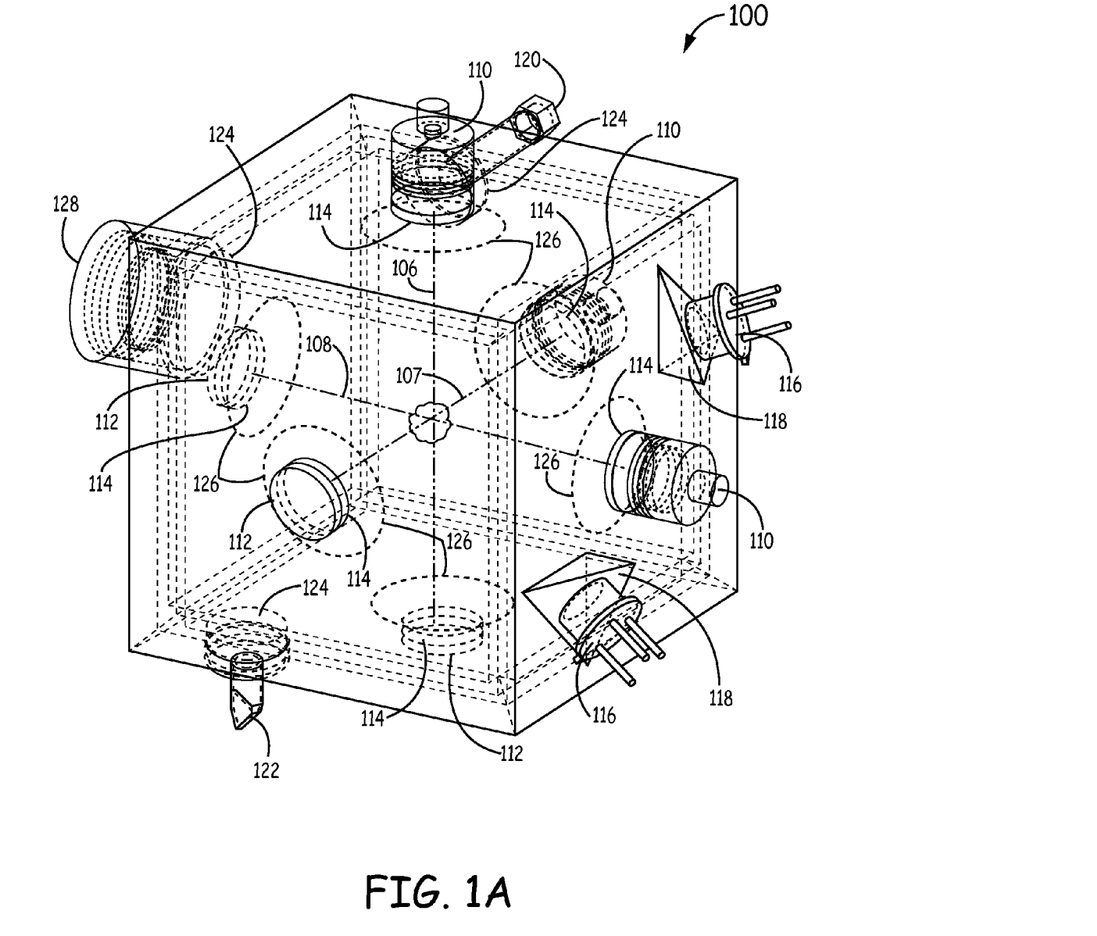
FIG. 1A is a perspective view of an example of a physics package of an atomic sensor apparatus.
Figure 1B:
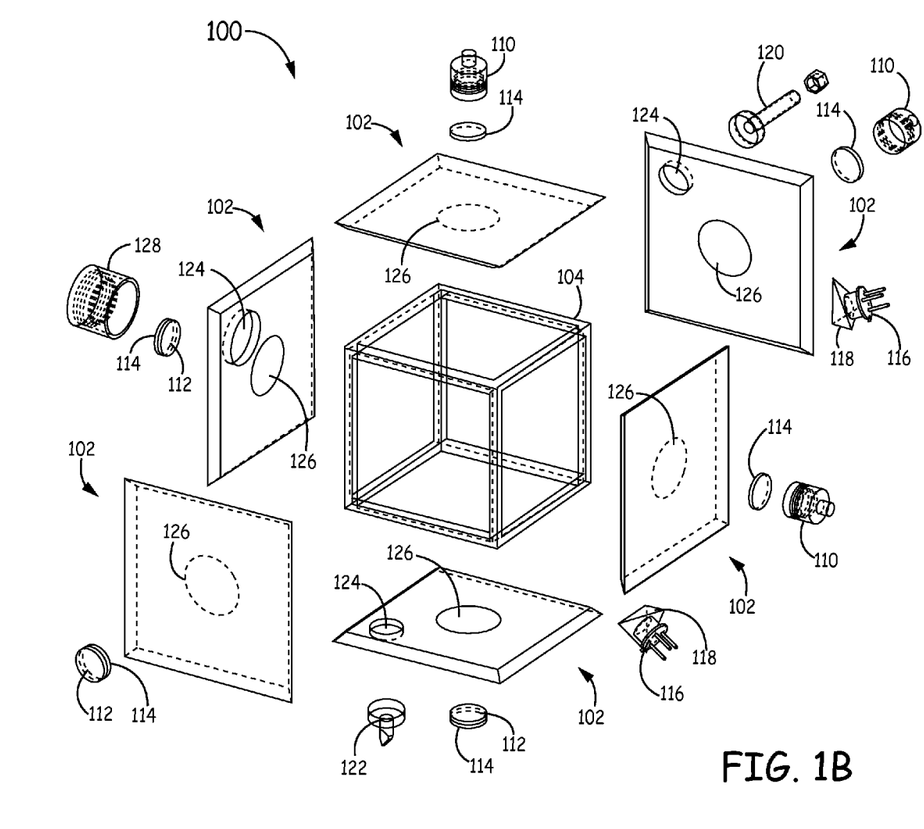
FIG. 1B is an exploded view of an example of a physics package of the atomic sensor apparatus of FIG. 1A.

FIG. 1A is a perspective view and FIG. 1B is an exploded view of an example of the physics package 100 of an atomic sensor apparatus. As shown, the physics package 100 includes a plurality of panes 102 of optically transparent material enclosing a vacuum chamber. In this example, the plurality of panes 102 are disposed to form a rectangular cuboid, specifically a cube. The plurality of panes 102 are fixedly attached together to form a hermetically sealed container defining the vacuum chamber therein. In other examples, the plurality of panes 102 can be disposed in other geometries such as in a pyramid.

Each pane 102 of the plurality of panes 102 is a planar structure having flat interior and exterior surfaces. The plurality of panes 102 can be fixedly attached together by being bonding to one another directly and/or by being bonded to a frame 104 as shown in FIG. 1B. The plurality of panes 102 can be bonded to one another or to a frame 104 with frit or sol gel.

The physics package can be used in an atomic sensor apparatus, such as an accelerometer or atomic clock. As known to those skilled in the art, such an atomic sensor operates by preparing a sample of cold atoms with light beams from one or more lasers; cold atoms serve as the basis of the sensor. While cold atom sensors are used in this example, sensors using thermal atomic samples would also benefit from the physics package 100 described herein. In a case of a clock, the atomic energy levels are spectroscopically interrogated by optical or microwave fields to compare and discipline the frequency output of an external oscillator to the atoms' internal energy levels. The physics package 100 defines a vacuum sealed chamber that contains the atoms that are interrogated. In an example, the atoms are alkali metal atoms, such as rubidium (e.g., Rb-87) or cesium and the vacuum sealed chamber is a passive vacuum with or without gettering agents. The physics package 100 described herein enables a plurality of light paths 106, 107, 108 from different angles to intersect with the same region within the physics package 100.

Atoms (e.g., an atom cloud) are slowed and cooled within the physics package 100 and collect at the intersection of the beams. Light beams from lasers can be propagated along the plurality of light paths 106, 107, 108 to intersect the atom cloud. These light beams can include light beams used to cool the atoms, and depending on the sensor operation, can include light beams used to interrogate or further manipulate the atoms.

In the example shown in FIGS. 1A and 1B, each of the three plurality of light waves 106, 107, 108 is generated by a separate light source 110. In one implementation of such an example, each of the light sources 110 are attached to a different pane 102 and each light source 110 is configured to direct a light beam perpendicularly through its respective pane. Each such light beam corresponds to one of the three intersecting light paths 106, 107, 108. Each light beam propagates from a respective light source 110, transmits through its respective pane 102, and over a respective light path 106, 107, 108. Each light beam is then incident on a pane 102 that is opposite the pane 102 to which the corresponding light source 110 is attached; the light beam is then retro-reflected back through the atom cloud toward its corresponding light source 110. In one implementation of such an example, the panes 102 are composed of glass and an external retro-reflective mirror 112 is attached to the pane 102 opposite each light source 110 to reflect each light beam back toward its light source 110. The incident lightwaves are circularly polarized with an external quarter waveplate 114 between the light source 110 and the first transmissive pane 102. An additional external quarter wave plate 114 is disposed between each retro-reflective mirror 112 and its corresponding pane 102 to rotate the polarization of the retro-reflective light beam.

Figure 2:
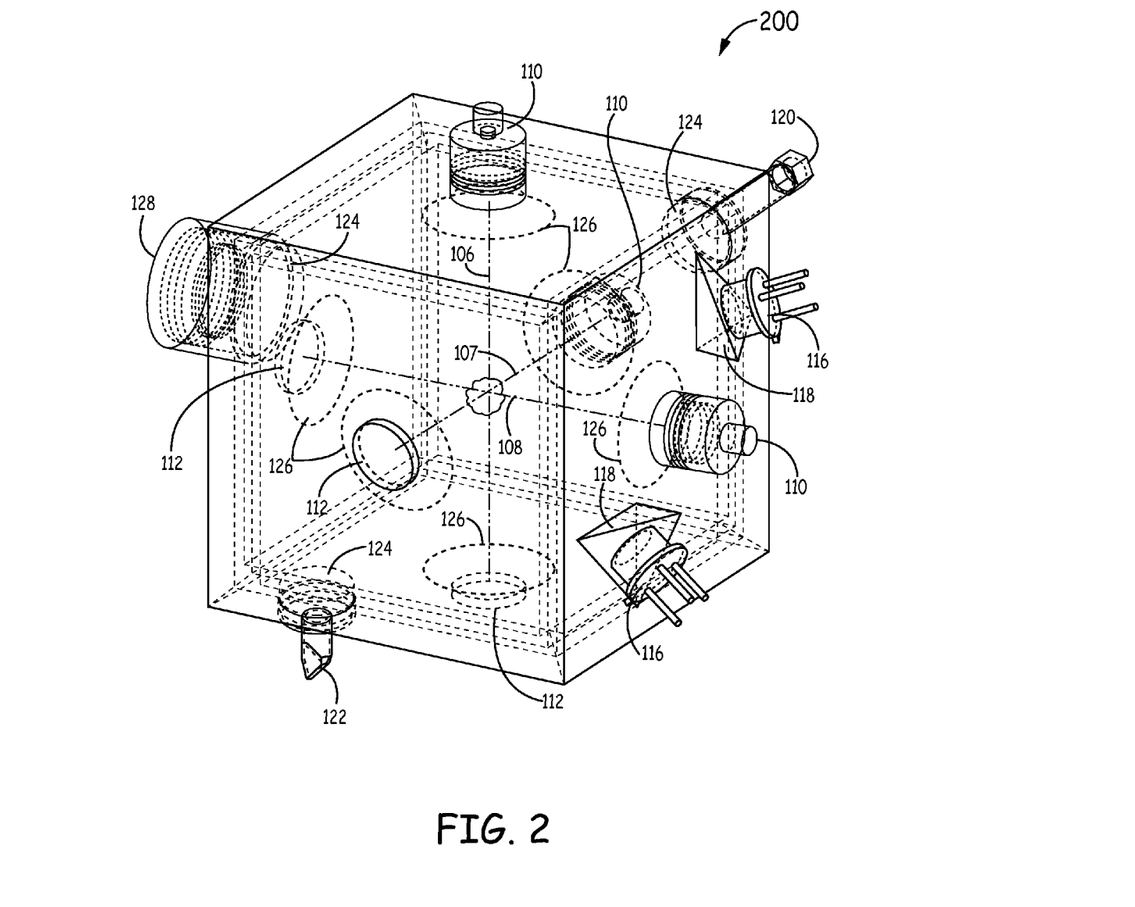
FIG. 2 is a perspective view of another example of a physics package of an atomic sensor apparatus.

In another example physics package 200 shown in FIG. 2, the panes 102 are composed of a naturally birefringent material, such as sapphire, to eliminate the need for external quarter wave plates 114. In such examples, the thickness of the pane 102 is carefully controlled to provide the appropriate polarization rotation upon passage through the pane 102. Moreover, in such an implementation, the retro-reflective mirrors 112 can be formed by a reflective coating on the pane 102 opposite each light source 110. For example, an interior surface of one or more panes 102 can be coated with a reflective film to form a mirror that can reflect light within the vacuum chamber. In one example, the entire interior surface of a pane 102 can be coated with a reflective film. In another example, only areas of the pane 102 which will be in or nearby the light path and reflecting the light beam can be coated with a reflective film. The reflective film can include a single or multilayer metal or dielectric stack coating. Other than the sapphire panes 102 and the lack of quarter wave plates 114, the physics package 200 is the same as the physics package 100 shown in FIGS. 1A and 1B.

As mentioned above, the light sources 110 are attached to respective panes 102 for generating the light beams for cooling and/or interrogation of the atoms. As an example, the light sources 110 can include a semiconductor laser such as a vertical cavity surface emitting laser (VCSEL), a distributed feedback laser, or an edge emitting laser.

In some examples, the light sources 110 can include a micro-fabricated vapor cell containing an alkali metal such as rubidium or cesium to provide absolute frequency stabilization of the light source(s) 110. The vapor cell containing an alkali metal is used to frequency stabilize the output from the light source(s) 110 to a predetermined atomic transition of the alkali metal. An atomic sensor including the physics package can also includes a plurality of magnetic field coils, such as a Helmholtz and anti-Helmholtz coils, for generating magnetic fields used for confining the atoms in the MOT and, as needed, in the operation of the atomic sensor.

In embodiments where the atomic sensor is a microwave atomic clock, a microwave crystal oscillator can be used to generate a microwave signal at the clock atomic transition of the alkali metal. The antenna or similar structure (e.g., a waveguide) is used to deliver the microwave signal from the local oscillator to perform spectroscopy on the alkali metal atoms of the physics package 100.

One or more light sources 110, photodetectors 116, and/or mirrors 112 disposed outside of the vacuum chamber and attached to one or more of the panes 102 can be configured to input, sense, or reflect light that transmits through a respective pane at an acute angle. In the examples shown in FIGS. 1A, 1B, and 2 the photodetectors 116 are configured to sense light that transmits through a corresponding pane 102 at an acute angle. The photodetectors 116 can be configured for fluorescence detection or for absorption detection depending on the desired use of the atomic sensor. To properly sense such an acute light beam, the photodetectors 116 are bonded to a wedge 118 which is then bonded to the pane 102. The wedge 118 can be an optically transparent solid structure, such as a prism, where the light propagates through the structure. The wedge 118 can also be hollow, where the light propagates through the hollow middle of the wedge. The wedge 118 can also be a mechanically adjustable mount such that the angle of the photodetector 116 can be adjusted after being attached to the pane 102 by adjusting the mechanically adjustable mount. The wedge 118 can also be a mechanically adjustable mount such that the angle of the photodetector 116 can be adjusted after being attached to the pane 102 by adjusting the mechanically adjustable mount. The mechanically adjustable mount can be configured to enable adjustment of the respective angle of mounting surfaces after mounting of the mechanically adjustable mount to a pane and a photodetector 116 or other component (e.g., light source 110, mirror 112).

The physics package 100 can also include a sample reservoir 120 and a vacuum chamber evacuation structure 122 attached to one or more of the panes 102. The sample reservoir 120 and vacuum chamber evacuation structure 122 can be attached over respective apertures 124 in the one or more panes 102. The sample reservoir 120 and the vacuum chamber evacuation structure 122 can be attached to the one or more panes 102 using frit or sol gel. The sample reservoir 120 can hold an alkali sample used to release atoms into the vacuum chamber for interrogation in the physics package 100. In an example, a mesh screen may be disposed across the aperture 124 in the pane 102 over which the sample reservoir 120 is attached to keep out larger chunks of broken glass in examples where the reservoir 120 is crushed to release the alkali sample. The chamber evacuation structure 122 is a hollow structure that provides an opening into the vacuum chamber. Such a chamber evacuation structure 122 can be used to perform initial evacuation of the vacuum chamber to ultra-high vacuum conditions. After evacuation of the vacuum chamber, the chamber evacuation structure 122 can be closed off to seal the vacuum chamber. In an example, the chamber evacuation structure 122 can be closed off by pinching the chamber evacuation structure 122. The chamber evacuation structure 122 and sample reservoir 120 can also serve as electrodes for forming a plasma for discharge cleaning of the physics package 100 and to enhance pump down and bake out.

Portions of or all of one or more panes 102 can be coated with an anti-reflective film to reduce unintended reflection of a light beam transmitting therethrough. The anti-reflective film can be coated on the inside and/or outside surface of the pane 102. In one example, the entire interior and/or exterior surface of a pane 102 can be coated with the anti-reflective film. In another example, only portions 126 of the pane 102 which will transmit a light beam into and/or out of the vacuum chamber can have an anti-reflective film coated thereon.

In some examples, a first portion of an interior surface of a pane 102 can have a reflective coating thereon and a second portion of the interior surface of the pane 102 can have an anti-reflective coating thereon. The first portion can correspond to a portion of the pane 102 in which a light path is incident and is to be reflected back into the vacuum chamber; that is, the reflective film can be coated on the portion that will be functioning as a mirror. The anti-reflective film can be placed on portions that will not be functioning as a mirror and/or portions that will be transmitting light into and/or out of the vacuum chamber.

In some examples, a polarization optic can be included between a light source 110, photodetector 116, or external mirror 112.

In an example, each pane 102 is composed of a glass, such as a glass-ceramic (e.g., Zerodur®) or an optical glass (e.g., BK-7), or another transparent material such as sapphire. In general each pane 102 should have the following properties: be vacuum tight, non-permeable to hydrogen or helium, non-reactive with the material to be introduced into the vacuum chamber, and, for transmissive panes, be low loss at the wavelength of interest. Other properties include low permeability to inert gases, such as Argon, and compatibility with frit bonding. In some examples, each pane 102 can be composed of a permeable material (or non-permeable material) that is enhanced with a non-permeable coating that, for example, does not alter the optical properties of the pane 102.

Some examples of the physics package 100 can include a gettering material within the vacuum sealed chamber to limit the partial pressures of some gasses (e.g., hydrogen). For example, a getter film can be applied, via sputtering or sintering, to an interior surface of the panes 102 that is not used as a reflective or transmissive surface before assembly. Such a getter can be activated after assembly, using proper activation temperature material, by laser heating from the outside of the physics package 100. Individual coatings, whether getter film, reflective, permeation prevention and/or other, can be applied to individual panes 102. In the example shown herein, a getter reservoir 128 is attached to one of the panes 102. The getter reservoir 128 can be attached over an appropriate aperture 124 in the pane 102. The getter reservoir 128 can be attached to the pane 102 using frit or sol gel. The getter reservoir 128 can hold a physical getter, such as barium, in a getter pan. The getter pan can be held inside a cylindrical glass chamber with a snap ring. The getter reservoir 128 is a hollow structure that provides an opening into the vacuum chamber.

In some examples as shown in FIG. 1B, one or more of the panes 102 can be attached to a frame 104. Such a frame 104 comprises a rigid structure including a plurality of slender support members extending between one another in a three-dimensional structure. The frame 104 can surround all or a portion of the vacuum chamber and can provide structure to hold the physical exterior of the vacuum chamber (e.g., the one or more panes 102) in place to form the vacuum chamber. The frame 104 can provide a structural framework for the one or more panes 102. That is, the frame 104 can act as a structure to which other components (e.g., the one or more panes 102) are attached and can define the physical relationship between the components when attached.

Figure 3:
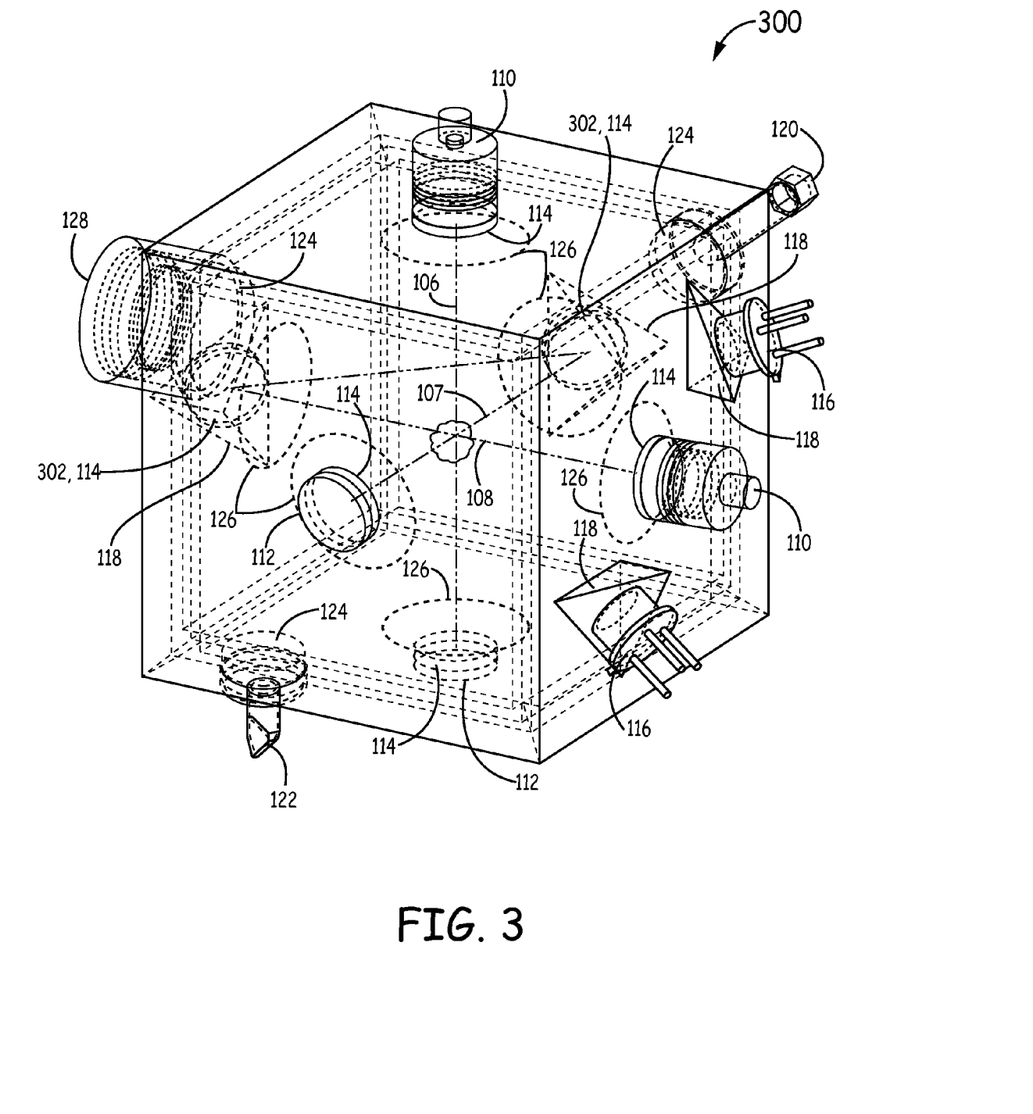
FIG. 3 is a perspective view of yet another example of a physics package of an atomic sensor apparatus.

FIG. 3 is a perspective view of another example physics package 300. The physics package 300 includes some similar components to the physics package 100 of FIG. 1, and these similar components have been numbered the same. The physics package 300 is configured to generate the three intersecting light beams using only two light sources 110. In order to do this, the light beam from one of the light sources 110 is reflected around the physics package along multiple (two) light paths 107, 108. The third light path 106 is generated with the light beam from a second light source 110 in the same manner as discussed with respect to FIG. 1A. To reflect a light beam from a light source 110 around the physics package the light source 110, folding mirrors 302, and/or retro-reflecting mirror 112 are mounted at an angle with respect to the pane 102 to which they are attached.

To propagate a light beam from the light source 110 that is oriented at an angle with respect to a first pane 102, a wedge 118 is disposed between the light source 110 and the first pane 102. The wedge 118 includes angled surfaces oriented to match the light source 110 and the first pane 102. The light source 110 is attached to the wedge 118 and the wedge 118 is attached to the exterior surface of the first pane 102. The light source 110, therefore, is fixedly attached to the first pane 102 via the prism.

A wedge 118 can also be disposed between the folding mirrors 302 and/or retro-reflecting mirror 112 to enable them to be mounted to the pane 102 at an angle. As described with respect to FIG. 1, the wedge 118 can include a prism, a hollow wedge, or a mechanically adjustable mount. By appropriately selecting the angle of the light source 110, the folding mirror 302, and the retro-reflecting mirror 112, the light beams can be directed along desired light paths (e.g., to produce both light path 107 and 108 with a single light beam). The folding mirrors 302 and/or retro-reflecting mirror 112 is attached to a wedge 118 and the wedge 118 is attached to respective panes 102.

Since the mirrors 112, 302 are external to the vacuum chamber, the light beam being reflected by the mirror 112, 302 transmits though a pane 102 and is then incident on the mirror 112, 302. After being reflected by the mirror 112, 302, the light beam is directed back towards the vacuum chamber, transmits back through the pane 102, and into the vacuum chamber. Advantageously, using a mirror 112, 302 that is external to the vacuum chamber enables the mirror 112, 302 to be aligned after fixedly attached of the panes 102 together to form the vacuum chamber. In an example, the mirror 112, 302 can be attached directly to a pane 102. In another example, the mirror 112, 302 can be attached to a wedge 118 and/or to a quarter wave plate 114 which is attached to a pane 102. The wedge 118 includes angled surfaces oriented to appropriate angle the mirror 112, 302 with respect to the pane 102. The reflective surfaces of an external mirror 112, 302 can be planar or curved to adjust a beam of light as necessary. As mentioned above, a reflective film on the interior surface of a pane 102 can be used instead of a retro-reflecting mirror 112 if the pane 102 is composed of a birefringent material such as sapphire.

The light sources 110, photodetectors 116, mirrors 112, 302, and/or wedges 118 can be attached to their respective panes 102 using frit or sol gel. If the a light source 110, photodetector 116, mirror 112, 302, and/or wedge 118 is not creating part of the vacuum seal for the vacuum chamber, the light source 110, photodetector 116, mirror 112, 302, and/or wedge 118 can be attached with frit, sol gel, a mechanical means, a UV epoxy, or other adhesive. A light source 110, photodetector 116, or mirror 112, 302, that is attached to a wedge 118 can be attached thereto using frit, sol gel, with a mechanical means, a UV epoxy, or other adhesive.

Since one or more of the light sources 110, photodetectors 116, and/or mirrors 112, 302, through the use of the wedges 118 can be mounted at an angle with respect to a pane 102, the geometry of the panes 102 is less limited by the light paths propagating therethrough. In particular, the orientation and placement of each pane 102 is not limited by the requirement that each light path enter and exit the vacuum chamber at a perpendicular angle with respect to a given pane 102. In contrast, a light path can enter or exit the vacuum chamber at an acute angle with respect to a pane 102. This permits more flexibility in the geometry formed by the panes 102; and, in particular, enables a geometry to be used that has increased strength and is more simple to manufacture. In an example, the vacuum chamber is defined by six or fewer panes 102. Accordingly, a geometry such as the cube shown in FIGS. 1A, 2, and 3 can be used.

The placement and orientation of the external mirrors 112, 302 and the light sources 110 is configured to provide the desired light paths within the vacuum chamber. For example, the placement and orientation of the external mirrors 112, 302 and light sources 110 can be configured to provide three light paths 106, 107, 108 that cross within the vacuum chamber of the physics package 100. In one implementation the three light paths 106, 107, 108 cross at approximately ninety (90) degree angles, however, this is not a requirement in all implementations. In the example shown in FIG. 3, two light beams are configured to collectively propagate along the three light paths 106, 107, 108. In another example, a single input light beam from a single light source 110 can be reflected around to propagate along the three light paths 106, 107, 108.

Figure 4:
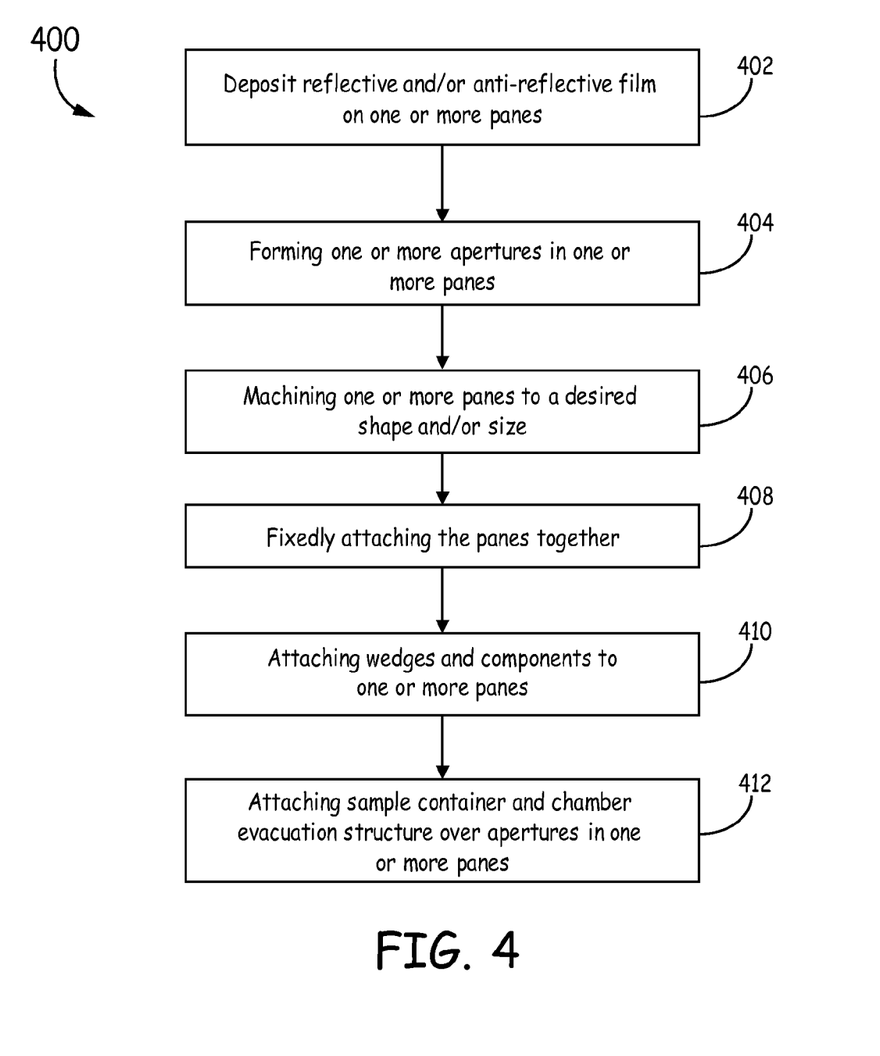
FIG. 4 is a flow chart of an example method of forming a physics package of the atomic sensor apparatus of any of FIGS. 1A-3.

FIG. 4 is a flow chart of an example method 400 of forming a physics package 100 for an atomic sensor apparatus 100, 200, 300. In some examples, an anti-reflective and/or reflective film can be placed on an interior and/or exterior surface of one or more of the panes 102 (block 402). The anti-reflective and/or reflective film can be placed on one or more of the panes 102 using any appropriate thin film deposition process. In implementations where the anti-reflective and/or reflective film is placed only on certain portions of a surface, a mask can be placed on the surface prior to applying the anti-reflective or reflective film, where the first mask does not cover portions in which the anti-reflective or reflective film are to be placed. Once the first mask has been deposited, the anti-reflective or reflective film can be deposited in the area(s) of the pane surface exposed by the first mask. The mask can then be stripped away. In implementations where a surface includes a reflective film on a first portion(s) and an anti-reflective film on other portion(s), a two-step mask process can be used. A first mask can be applied, where the portions in which the reflective film is to be placed are not covered by the first mask. The reflective film can then be applied to the areas exposed by the first mask on the surface. The first mask can then be stripped away. Next, a second mask can be applied, where the second mask does not cover portions in which the anti-reflective film is to be placed. Presumably, the second mask would cover the portion(s) of the surface in which the reflective film was applied, such that the anti-reflective film is not applied over the reflective film. The anti-reflective film can then be applied in the area(s) of the pane surface exposed by the second mask. The second mask can then be stripped away. The two-step process can also be implemented in the opposite order with the anti-reflective film being applied first and the reflective film being applied second. The locations of the anti-reflective film and/or reflective film can be selected as locations in which a light beam is to be transmitted through or reflected off of a pane 102 as discussed above. In some examples anti-reflective film and/or reflective film applied to an interior surface of a pane 102 can be applied prior to fixedly attached of the panes 102 (block 408), and anti-reflective and/or reflective film applied to an exterior surface of a pane 102 can be applied after fixedly attached of the panes 102. In another example, anti-reflective and/or reflective film on the exterior surface of a pane 102 can also be applied prior to mechanical coupling of the panes 102.

One or more apertures 124 can be formed in one or more panes 102 for the sample reservoir 120, vacuum chamber evacuation structure 122, and/or getter reservoir 128 (block 404). Such aperture(s) 124 can be formed prior to or after fixedly attaching of the panes 102 (block 408). The aperture(s) 124 can be formed using any appropriate method such as cutting or etching a pane 102.

One or more of the panes 102 can be machined or etched to a desired shape and/or size (block 406). In an example, each pane 102 can be machined or etched into a generally rectangular shape as shown in FIGS. 1A, 1B, 2, and 3. In other examples, other shapes can be used. The panes 102 may also be polished to remove surface roughness for better transmission of light beams with less distortion or scatter. The simple geometry of the panes 102 described herein enables easier polishing of the surfaces.

The plurality of panes 102 can be fixedly attached together to form the vacuum chamber (block 408). The plurality of panes 102 can be fixedly attached together to form the desired geometry such as a rectangular cuboid (e.g., a cube). In other examples, other geometries can be formed. In an example, the plurality of panes 102 can be fixedly attached together by directly bonding the panes 102 to one another. In another example, the plurality of panes 102 can be fixedly attached together by bonding the plurality of panes 102 to a frame 104. In yet another example, the plurality of panes 102 can have some edges bonded to other panes 102 and other edges that are bonded to a frame 104. Any appropriate bonding technique can be used, such as a frit seal or sol gel. The panes 102 are fixedly attached together in a manner that achieves a vacuum tight seal for the vacuum chamber. Appropriate panes 102 (e.g., having anti-reflective films 126, reflective films, and/or apertures 124 in particular locations) can be placed in appropriate positions to achieve the desired light paths and configuration of the vacuum chamber.

The light sources 110, photodetectors 116, and/or mirrors 112, 302 along with any wedges 118 can be attached to one or more of the panes 102 (block 410). Attaching the light sources 110, photodetectors 116, and/or mirrors 112, 302 along with any wedges 118 can include attaching light sources 110, photodetectors 116, and/or mirrors 112, 302 directly to one or more panes 102. Attaching the light sources 110, photodetectors 116, and/or mirrors 112, 302 along with any wedges 118 can also include attaching one or more of the wedges 118 to a respective light source 110, photodetector 116, and/or mirror 112, 302, and attaching the wedge 118 to one or more panes 102.

Attaching the light sources 110, photodetectors 116, and/or mirrors 112, 302 along with any wedges 118 can also include aligning the light sources 110, photodetectors 116, and/or mirrors 112, 302 along with any wedges 118 with a desired light path and/or other reference. This aligning can include attaching the light sources 110, photodetectors 116, and/or mirrors 112, 302 along with any wedges 118 at appropriate orientations and in appropriate locations on an exterior surface of one or more of the panes 102 to achieve the desired light paths. Aligning the light sources 110, photodetectors 116, and/or mirrors 112, 302 along with any wedges 118 can also include aligning with a portion(s) of a pane having anti-reflective film or reflective film thereon to achieve the desired light paths. The light sources 110, photodetectors 116, and/or mirrors 112, 302 along with any wedges 118 can be attached using an appropriate bonding technique such as a frit seal, sol gel, a mechanical means, a UV epoxy, or other adhesive. In some examples, one or more a light sources 110, photodetectors 116, and/or mirrors 112, 302 can also be attached to a wedge 118 using a frit seal, sol gel, a mechanical means, a UV epoxy, or other adhesive.

The sample reservoir 120, chamber evacuation structure 122, and/or getter reservoir 128 can also be attached over respective apertures in one or more panes 102 (block 412). The sample reservoir 120, chamber evacuation structure 122, and/or getter reservoir 128 can be attached using an appropriate bonding technique such as a frit seal or sol gel. The sample reservoir 120, chamber evacuation structure 122, and/or getter reservoir 128 can be attached in a manner that achieves a vacuum tight seal for the vacuum chamber.

Example Embodiments

Example 1 includes a physics package of an atomic sensor, the physics package comprising: a plurality of panes of optically transparent material enclosing a vacuum chamber; one or more wedges attached to an external surface of one or more of the panes; and at least one of a light source, photodetector, or mirror attached to the one or more wedges, the light source configured to generate an input light beam for the vacuum chamber, the photodetector configured to detect an output light beam from the vacuum chamber, and the mirror configured to reflect a light beam from the vacuum chamber back into the vacuum chamber, wherein the wedge is configured to oriented such a light source, photodetector, or mirror such that a respective light beam corresponding thereto transmits through a corresponding pane at an acute angle with respect to the corresponding pane.

Example 2 includes the physics package of Example 1, wherein the plurality of panes comprise six or fewer panes.

Example 3 includes the physics package of Example 2, wherein the plurality of panes are disposed in a rectangular cuboid geometry.

Example 4 includes the physics package of any of Example 1-4, wherein one or more of the panes include an anti-reflective coating on an interior or exterior surface thereof.

Example 5 includes the physics package of any of Example 1-5, wherein one or more of the panes include a reflective coating on an interior surface thereof.

Example 6 includes the physics package of any of Example 1-5, wherein the one or more wedges include a prism.

Example 7 includes the physics package of any of Example 1-5, wherein the one or more wedges include a hollow wedge, wherein a corresponding light beam is configured to propagate through a hollow middle of the hollow wedge.

Example 8 includes the physics package of any of Example 1-5, wherein the one or more wedges include a mechanically adjustable mount configured to alter an angle of a component mounted thereto with respect to a pane when the mechanically adjustable mount is adjusted.

Example 9 includes the physics package of any of Example 1-8, wherein the plurality of panes are at least one of bonded to a frame or bonded to one another.

Example 10 includes the physics package of any of Example 1-9, wherein the plurality of panes are composed of glass, glass-ceramic, optical glass, or sapphire.

Example 11 includes the physics package of any of Example 1-10, wherein one or more of the panes include an aperture for attachment of a sample reservoir, an evacuation structure, or a getter reservoir.

Example 12 includes a method of forming a physics package, the method comprising: fixedly attaching a plurality of panes of optically transparent material together to form a vacuum chamber; attaching one or more wedges to an external surface of one or more of the panes; and attaching at least one of a light source, photodetector, or mirror to the one or more wedges, the light source configured to generate an input light beam for the vacuum chamber, the photodetector configured to detect an output light beam from the vacuum chamber, and the mirror configured to reflect a light beam from the vacuum chamber back into the vacuum chamber; wherein attaching one or more wedges and attaching at least one of a light source, photodetector, or mirror to the one or more wedges includes aligning the one or more wedges and the at least one of a light source, photodetector, or mirror such that one or more beams of light enter the vacuum chamber and are reflected to form three light paths that cross within the vacuum chamber and at least one light path transmits through a pane at an acute angle with respect to the pane.

Example 13 includes the method of Example 12, wherein fixedly attaching the plurality of panes together includes forming a rectangular cuboid geometry with the plurality of panes.

Example 14 includes the method of any of Example 12 or 13, wherein fixedly attaching the plurality of panes together includes at least one of bonding panes to a frame and bonding panes to one another.

Example 15 includes the method of any of Example 12-14, comprising: coating at least one of an interior or exterior surface of at least one of the plurality of panes with an anti-reflective film.

Example 16 includes the method of any of Example 12-15, wherein the one or more wedges include a prism.

Example 17 includes the method of any of Example 12-15, wherein the one or more wedges include a hollow wedge, wherein a corresponding light beam is configured to propagate through a hollow middle of the hollow wedge.

Example 18 includes a physics package of an atomic sensor, the physics package comprising: a plurality of panes of optically transparent material disposed in a rectangular cuboid geometry enclosing a vacuum chamber; one or more wedges attached to an external surface of one or more of the panes; at least one of a light source, photodetector, or mirror attached to the one or more wedges, the light source configured to generate an input light beam for the vacuum chamber, the photodetector configured to detect an output light beam from the vacuum chamber, and the mirror configured to reflect a light beam from the vacuum chamber back into the vacuum chamber; wherein the at least one of a light source, photodetector, or mirror and the one or more prisms are disposed such that one or more beams of light enter the vacuum chamber and are reflected to form three light paths that cross within the vacuum chamber and at least one light path transmits through a pane at an acute angle with respect to the pane; a getter reservoir attached to a first of the plurality of panes over an aperture defined in the first of the plurality of panes; and frit or sol gel on edges of the plurality of panes, hermetically sealing the vacuum chamber.

Example 19 includes the physics package of Example 18, wherein the one or more wedges include a prism.

Example 20 includes the physics package of Example 18, wherein the one or more wedges include a hollow wedge, wherein a corresponding light beam is configured to propagate through a hollow middle of the hollow wedge.

What is claimed is:

1. A physics package of an atomic sensor, the physics package comprising:
    a plurality of panes of optically transparent material enclosing a vacuum chamber, wherein the plurality of panes are fixedly attached together to form a hermetically sealed container defining the vacuum chamber therein;
    one or more wedges attached to an external surface of one or more of the panes;
    at least one of a light source, photodetector, or mirror attached to the one or more wedges, the light source configured to generate an input light beam for the vacuum chamber, the photodetector configured to detect an output light beam from the vacuum chamber, and the mirror configured to reflect a light beam from the vacuum chamber back into the vacuum chamber;
    wherein the one or more wedges are configured to oriente such a light source, photodetector, or mirror such that a respective light beam corresponding thereto transmits through a corresponding pane at an acute angle with respect to the corresponding pane;
    and
    wherein the at least one of a light source, photodetector, or mirror, and the one or more wedges is oriented such that one or more beams of light enter the vacuum chamber and are reflected to form at least three light paths that cross within the vacuum chamber.

2. The physics package of claim 1, wherein the plurality of panes comprise six or fewer panes.

3. The physics package of claim 2, wherein the plurality of panes are disposed in a rectangular cuboid geometry.

4. The physics package of claim 1, wherein one or more of the panes include an anti-reflective coating on an interior or exterior surface thereof.

5. The physics package of claim 1, wherein one or more of the panes include a reflective coating on an interior surface thereof.

6. The physics package of claim 1, wherein the one or more wedges include a prism.

7. The physics package of claim 1, wherein the one or more wedges include a hollow wedge, wherein a corresponding light beam is configured to propagate through a hollow middle of the hollow wedge.

8. The physics package of claim 1, wherein the one or more wedges include a mechanically adjustable mount configured to alter an angle of a component mounted thereto with respect to a pane when the mechanically adjustable mount is adjusted.

9. The physics package of claim 1, wherein the plurality of panes are at least one of bonded to a frame or bonded to one another.

10. The physics package of claim 1, wherein the plurality of panes are composed of glass, glass-ceramic, optical glass, or sapphire.

11. The physics package of claim 1, wherein one or more of the panes include an aperture for attachment of a sample reservoir, an evacuation structure, or a getter reservoir.

12. A method of forming a physics package, the method comprising:
    fixedly attaching a plurality of panes of optically transparent material together to form a hermetically sealed container defining a vacuum chamber therein;
    attaching one or more wedges to an external surface of one or more of the panes; and
    attaching at least one of a light source, photodetector, or mirror to the one or more wedges, the light source configured to generate an input light beam for the vacuum chamber, the photodetector configured to detect an output light beam from the vacuum chamber, and the mirror configured to reflect a light beam from the vacuum chamber back into the vacuum chamber;
    wherein attaching one or more wedges and attaching at least one of a light source, photodetector, or mirror to the one or more wedges includes aligning the one or more wedges and the at least one of a light source, photodetector, or mirror such that one or more beams of light enter the vacuum chamber and are reflected to form three light paths that cross within the vacuum chamber and at least one light path transmits through a pane at an acute angle with respect to the pane.

13. The method of claim 12, wherein fixedly attaching the plurality of panes together includes forming a rectangular cuboid geometry with the plurality of panes.

14. The method of claim 12, wherein fixedly attaching the plurality of panes together includes at least one of bonding panes to a frame and bonding panes to one another.

15. The method of claim 12, comprising:
    coating at least one of an interior or exterior surface of at least one of the plurality of panes with an anti-reflective film.

16. The method of claim 12, wherein the one or more wedges include a prism.

17. The method of claim 12, wherein the one or more wedges include a hollow wedge, wherein a corresponding light beam is configured to propagate through a hollow middle of the hollow wedge.

18. A physics package of an atomic sensor, the physics package comprising:
    a plurality of panes of optically transparent material disposed in a rectangular cuboid geometry enclosing a vacuum chamber;
    one or more wedges attached to an external surface of one or more of the panes;
    at least one of a light source, photodetector, or mirror attached to the one or more wedges, the light source configured to generate an input light beam for the vacuum chamber, the photodetector configured to detect an output light beam from the vacuum chamber, and the mirror configured to reflect a light beam from the vacuum chamber back into the vacuum chamber;

wherein the at least one of a light source, photodetector, or mirror and the one or more prisms are disposed such that one or more beams of light enter the vacuum chamber and are reflected to form three light paths that cross within the vacuum chamber and at least one light path transmits through a pane at an acute angle with respect to the pane;

a getter reservoir attached to a first of the plurality of panes over an aperture defined in the first of the plurality of panes; and frit or sol gel on edges of the plurality of panes, hermetically sealing the vacuum chamber.

19. The physics package of claim 18, wherein the one or more wedges include a prism.

20. The physics package of claim 18, wherein the one or more wedges include a hollow wedge, wherein a corresponding light beam is configured to propagate through a hollow middle of the hollow wedge.

\* \* \* \* \*